(12) United States Patent
Ferdosi et al.

(10) Patent No.: US 11,406,328 B2
(45) Date of Patent: Aug. 9, 2022

(54) LOW-DISTORTION ECG DENOISING

(71) Applicant: Vital Connect, Inc., San Jose, CA (US)

(72) Inventors: Nima Ferdosi, Campbell, CA (US); Ravi Narasimhan, Campbell, CA (US)

(73) Assignee: Vital Connect, Inc., San Jose, CA (US)

( * ) Notice: Subject to any disclaimer, the term of this patent is extended or adjusted under 35 U.S.C. 154(b) by 700 days.

(21) Appl. No.: 16/285,578

(22) Filed: Feb. 26, 2019

(65) Prior Publication Data

US 2019/0183425 A1 Jun. 20, 2019

Related U.S. Application Data

(60) Continuation of application No. 15/972,342, filed on May 7, 2018, now Pat. No. 10,213,163, which is a division of application No. 14/089,342, filed on Nov. 25, 2013, now Pat. No. 9,986,951.

(51) Int. Cl.
| | |
|---|---|
| *A61B 5/00* | (2006.01) |
| *A61B 5/316* | (2021.01) |
| *A61B 5/352* | (2021.01) |
| *A61B 5/366* | (2021.01) |

(52) U.S. Cl.
CPC .......... *A61B 5/7203* (2013.01); *A61B 5/0006* (2013.01); *A61B 5/316* (2021.01); *A61B 5/352* (2021.01); *A61B 5/366* (2021.01)

(58) Field of Classification Search
CPC .............................. A61B 5/0006; A61B 5/7203
USPC ......................................... 600/301, 517; 607/9
See application file for complete search history.

(56) References Cited

U.S. PATENT DOCUMENTS

| | | |
|---|---|---|
| 5,560,368 A | 10/1996 | Berger |
| 2008/0294019 A1 | 11/2008 | Tran |
| 2013/0085405 A1 | 4/2013 | Bera et al. |

*Primary Examiner* — Nadia A Mahmood
(74) *Attorney, Agent, or Firm* — Brundidge & Stanger, P.C.

(57) ABSTRACT

A method and system for low-distortion denoising of an ECG signal are disclosed. The method comprises determining at least one beat of the ECG signal for denoising using a beat selection logic and denoising the at least one beat using at least one ensemble averaging filter. The system includes a sensor to detect the ECG signal, a processor coupled to the sensor, wherein the processor includes a beat selection logic unit, and a memory device coupled to the processor, wherein the memory device includes an application that, when executed by the processor, causes the processor to determine at least one beat of the ECG signal for denoising using a beat selection logic and to denoise the at least one beat using at least one ensemble averaging filter.

20 Claims, 10 Drawing Sheets

LOW-DISTORTION ECG DENOISING

CROSS-REFERENCE TO RELATED APPLICATIONS

This application is a Continuation of U.S. Ser. No. 15/972,342, filed May 7, 2018; which is a Divisional under 35 U.S.C. § 120 of U.S. patent application Ser. No. 14/089,342, filed on Nov. 25, 2013. The disclosure of the application is hereby incorporated herein by reference in its entirety.

FIELD OF THE INVENTION

The present invention relates to wireless sensor devices, and more particularly, to low-distortion denoising of an ECG signal detected by the wireless sensor devices.

BACKGROUND

Wireless sensor devices are used in a variety of applications including the health monitoring of users. In many of these health monitoring applications, a wireless sensor device is attached directly to the user's skin (e.g. upper-body chest area) to measure certain data (e.g. an electrocardiogram ECG signal). The wireless sensor device is also capable of detecting other conditions (e.g. posture, respiratory rate). Duration, amplitude and features of the ECG signal sections (e.g. entire ECG waveform, QRS complex, T Wave, etc.) contain valuable information about the cardiovascular health of the user and therefore should be preserved.

However, several ambient noises such as motion artifacts, baseline wander, and muscle artifact, potentially caused by the movement of the user, are mixed with the ECG signal and are thus detected by conventional wireless sensor devices. Accordingly, these ambient noises as well as conventional triboelectic filtering result in a distortion of the ECG signal. Therefore, there is a strong need for a cost-effective and efficient solution that overcomes the aforementioned issues. The present invention addresses such a need.

SUMMARY OF THE INVENTION

A method and system for low-distortion denoising of an ECG signal are disclosed. The method comprises determining at least one beat of the ECG signal for denoising using a beat selection logic and denoising the at least one beat using at least one ensemble averaging filter.

The system includes a sensor to detect the ECG signal, a processor coupled to the sensor, wherein the processor includes a beat selection logic unit, and a memory device coupled to the processor, wherein the memory device includes an application that, when executed by the processor, causes the processor to determine at least one beat of the ECG signal for denoising using a beat selection logic and to denoise the at least one beat using at least one ensemble averaging filter.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present invention.

DETAILED DESCRIPTION

The present invention relates to wireless sensor devices, and more particularly, to low-distortion denoising of an ECG signal detected by the wireless sensor devices. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

In one embodiment, a wireless sensor device with an embedded sensor and electrodes is attached to a user to detect an electrocardiogram (ECG) signal (e.g. a single-lead, bipolar ECG signal) and other health conditions (e.g. posture). The analog ECG signal is filtered by a fixed analog anti-aliasing filter before the analog ECG signal is sampled and converted to a digital domain through an Analog to Digital converter (ADC) and passed to a signal processing unit of the wireless sensor device for the extraction of health related data including but not limited to a RR interval, heart rate, heart rate variability and other ECG signal features. Aside from being used to measure heart related data, the wireless sensor device also records a digitized ECG waveform that is used by a physician to make various diagnoses.

A method and system in accordance with the present invention reduces signal noise and corruption such as baseline wander, motion artifacts, and muscle noise in the ECG signal without distorting or altering the valuable ECG signal features via a wireless sensor device. In one embodiment, the wireless sensor device reduces the signal noises by detecting a QRS peak of an ECG signal, performing baseline cancellation by reconstructing baseline noise of the ECG signal, storing a last N beats of the ECG signal, stretching every beat of the last N beats in time-domain to create a resampled beat with a constant length in seconds, aligning the stretched beats to align peaks of the stretched beats in time, comparing ECG beat characteristics, and scaling back beat length of the last N beats to an original length.

In one embodiment, N includes but is not limited to 16 and the constant length includes but is not limited to LENGTH_REFERENCE_BEAT seconds. In another embodiment, the comparing step further comprises determining if an ECG beat is close enough in characteristics to neighboring beats for denoising or not and if yes (the ECG beat is close enough in characteristics to neighboring beats), using ensemble averaging with appropriate parameters for each section of the ECG beat to reduce noise at different sections of every beat of the last N beats of the EGG signal.

Figure 1:
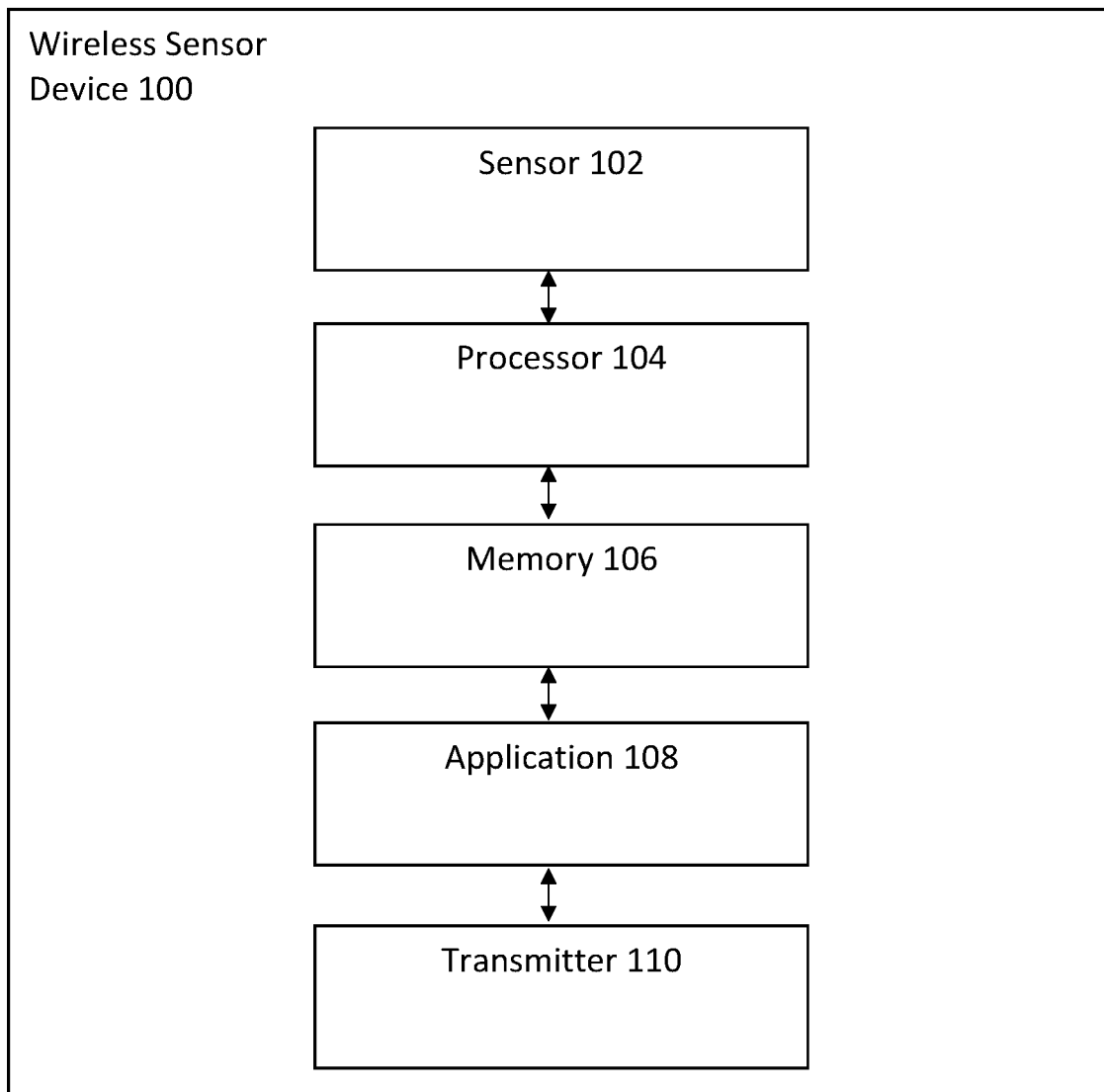
FIG. 1 illustrates a wireless sensor device for low-distortion denoising of an ECG signal in accordance with an embodiment.

FIG. 1 illustrates a wireless sensor device 100 for low-distortion ECG denoising in accordance with an embodiment. The wireless sensor device 100 includes a sensor 102, a processor 104 coupled to the sensor 102, a memory 106 coupled to the processor 104, an application 108 coupled to the memory 106, and a transmitter 110 coupled to the application 108. In one embodiment, the wireless sensor device 100 is attached to a user to detect an EGG signal via the sensor 102. The sensor 102 obtains data from the user which is transmitted to the memory 106 in turn to the application 108 via the processor 104. The processor 104 executes the application 108 to obtain information regarding the user's health. The information is transmitted to the transmitter 110 and in turn relayed to another user or device.

In one embodiment, the sensor 102 is any of a microelectromechanical system (MEMS) tri-axial accelerometer and an embedded sensor with electrodes and the processor 104 is a microprocessor. One of ordinary skill in the art readily recognizes that a variety of devices can be utilized for the sensor 102, the processor 104, the memory 106, the application 108, and the transmitter 110 and that would be within the spirit and scope of the present invention. Additionally, one of ordinary skill in the art readily recognizes that a variety of wireless sensor devices can be utilized including but not limited to a wireless sensor device in a patch form-factor, tri-axial accelerometers, uni-axial accelerometers, bi-axial accelerometers, gyroscopes, and pressure sensors and that would be within the spirit and scope of the present invention.

To describe the features of the present invention in more detail, refer now to the following description in conjunction with the accompanying Figures.

Figure 2:
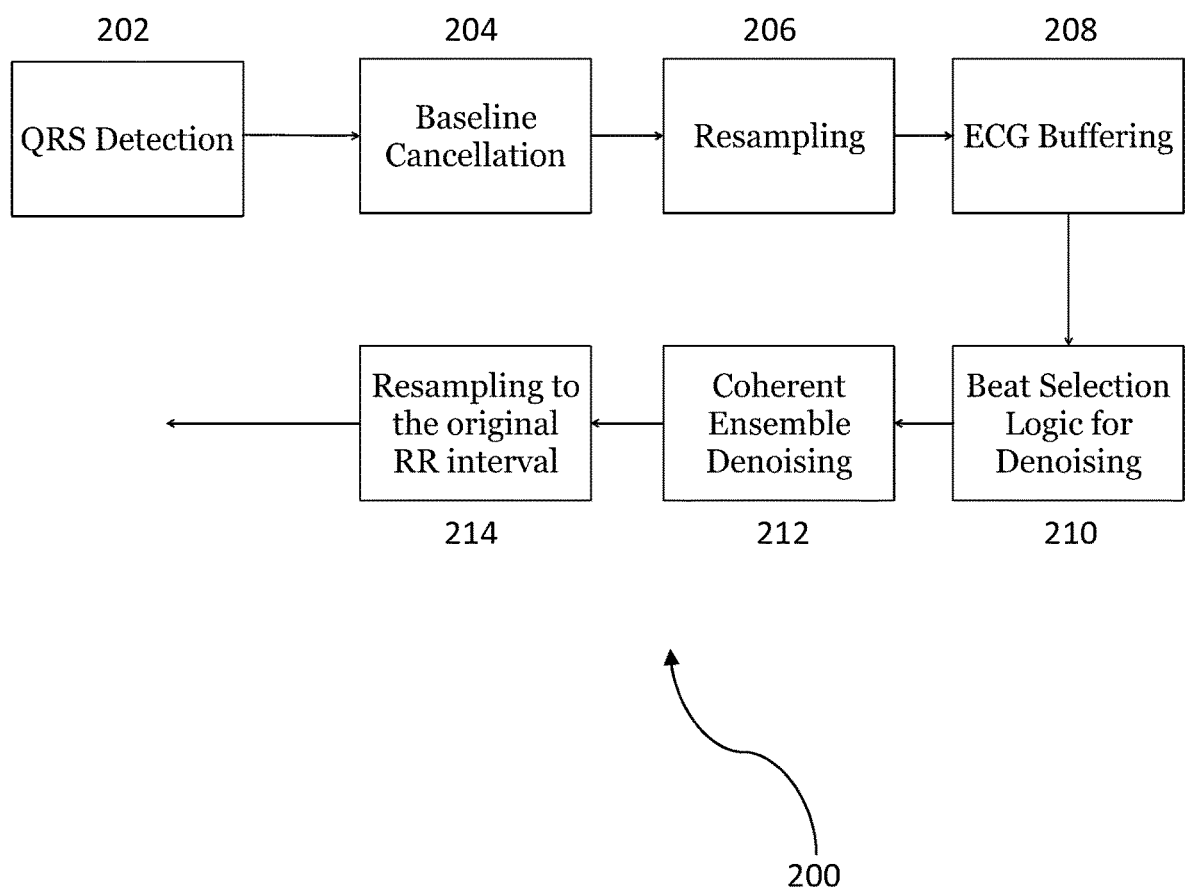
FIG. 2 illustrates a method for low-distortion denoising of an ECG signal in accordance with an embodiment.

FIG. 2 illustrates a method 200 for low-distortion denoising of an ECG signal by a wireless sensor device in accordance with an embodiment. The method 200 includes QRS detection via step 202, baseline cancellation via step 204, resampling via step 206, storing the last N beats of the ECG signal (ECG buffering) via step 208, beat selection logic for denoising via step 210, coherent ensemble denoising via step 212, and resampling to the original RR interval via step 214.

In one embodiment, the QRS detection via step 202 comprises detecting at least one QRS complex peak from an original ECG signal detected by the wireless sensor device. The ECG signal is filtered to remove low-frequency noise sources including but not limited to baseline wander and high frequency noise sources including but not limited to motion artifacts and power-line noise. In another embodiment, the ECG signal is filtered using an aggressive (narrow bandwidth) band-pass filter. In this embodiment, the narrow bandwidth band-pass filtered ECG signal is only used for ORS detection of step 202 and the wireless sensor device processes steps 204-214 using the original ECG signal.

Figure 3:
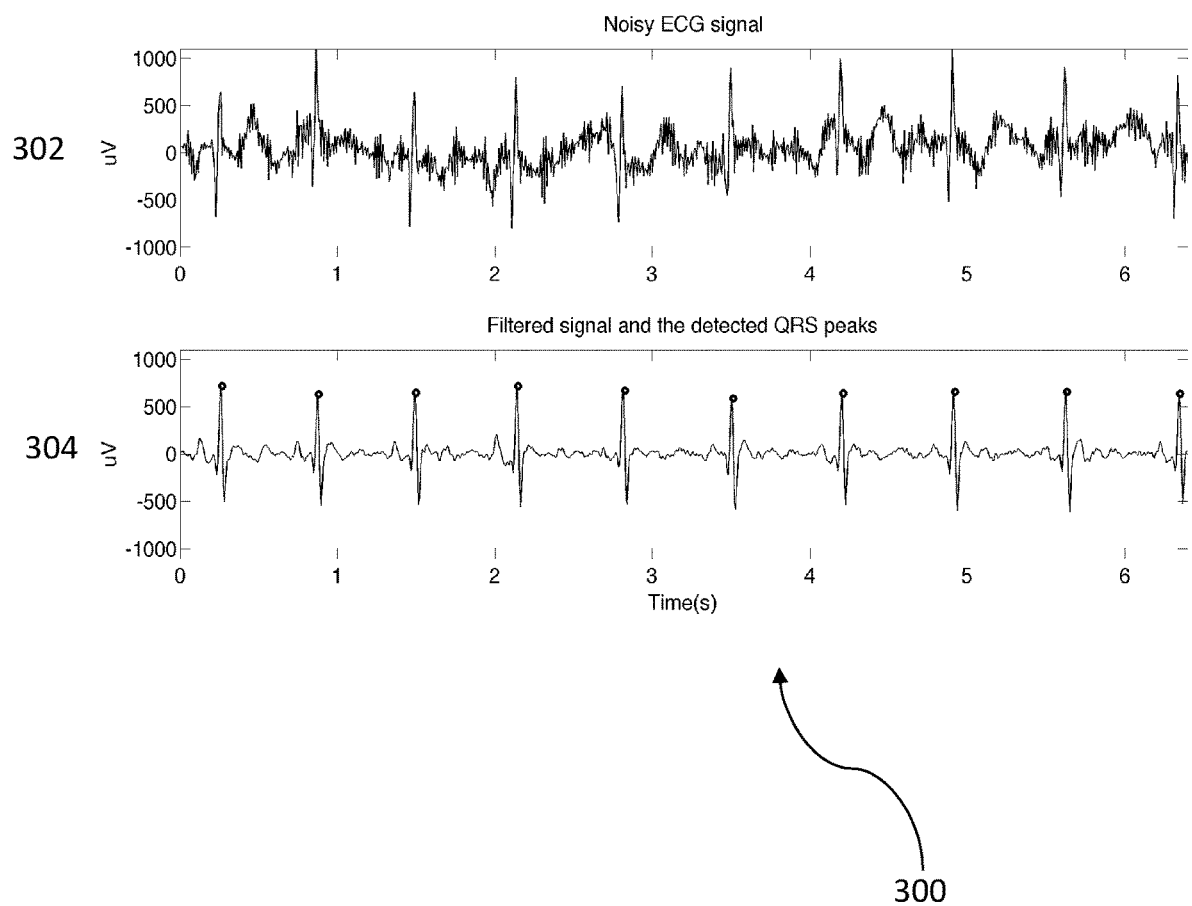
FIG. 3 illustrates a diagram of ECG signals in accordance with an embodiment.
Figure 4:
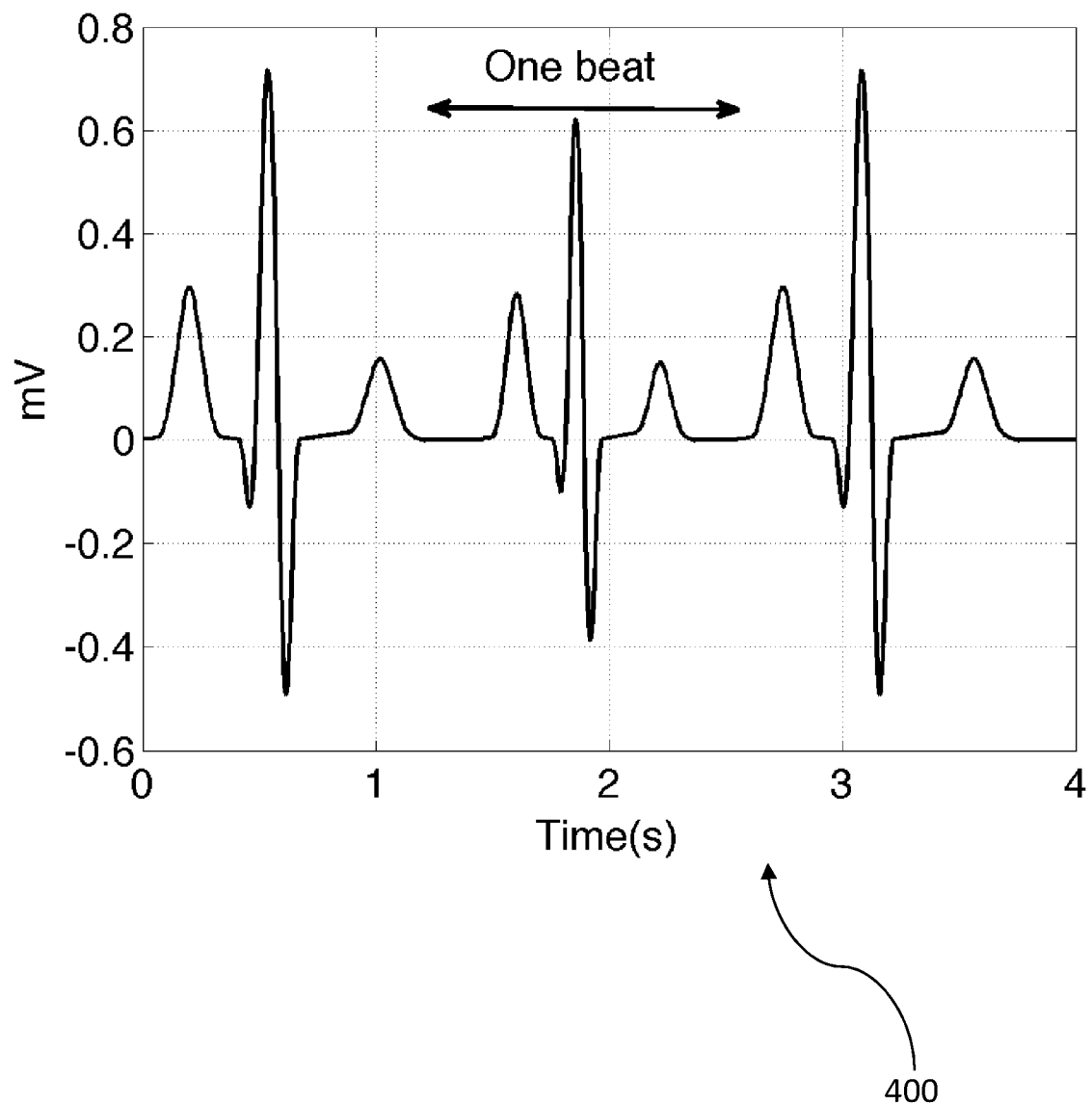
FIG. 4 illustrates a zoomed view of a diagram of an ECG signal in accordance with an embodiment.

FIG. 3 illustrates a diagram 300 of ECG signals in accordance with an embodiment. The diagram 300 includes a first graph 302 depicting a noisy ECG signal 302 and a second graph 304 depicting a filtered ECG signal and detected QRS complex peaks. FIG. 4 illustrates a zoomed view of a diagram 400 of an ECG signal in accordance with an embodiment. The diagram 400 depicts one heart beat within the ECG signal that is plotted over time.

Baseline cancellation can be achieved by filtering the ECG signal with a high-pass filter. However, using a high-pass filter for baseline cancelation results in distortion of ECG features (e.g. ST-segment) because a large portion of the baseline wander noise is in the same band as the ECG features. In one embodiment, the baseline cancellation via step 204 comprises filtering the ECG signal with a low-distortion method for baseline cancellation. The low-distortion method calculates baseline wander noise during beats of the ECG signal by interpolating between values of the TP segment of consecutive beats.

Figure 5:
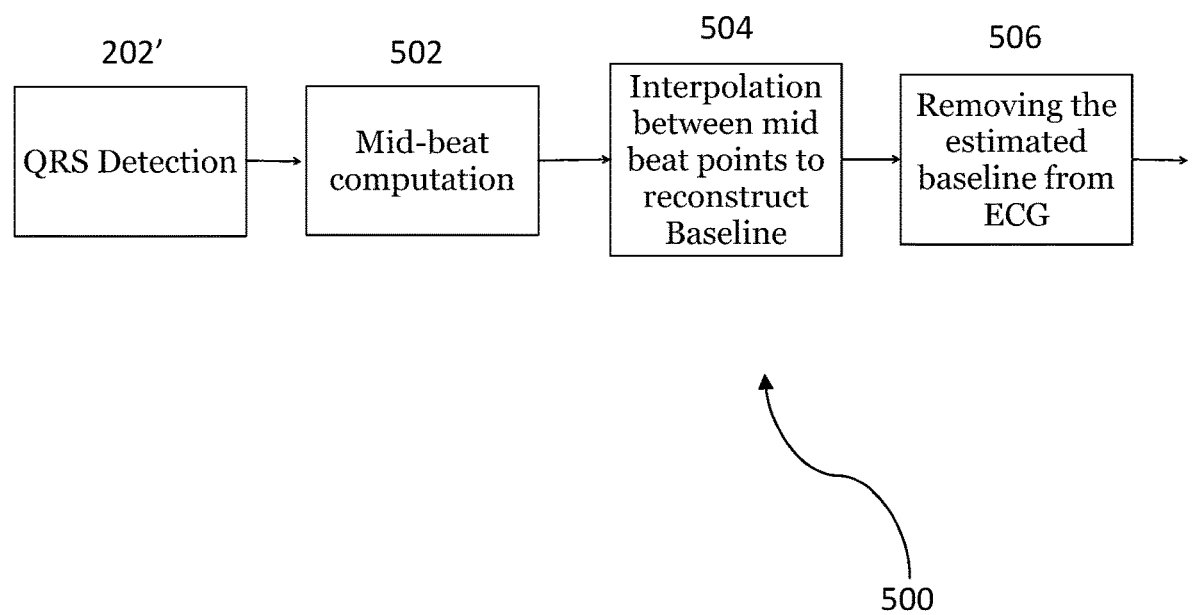
FIG. 5 illustrates a method for low-distortion baseline cancellation in accordance with an embodiment.

FIG. 5 illustrates a method 500 for low-distortion baseline cancellation in accordance with an embodiment. The method 500 includes the wireless sensor device detecting a QRS complex peak via step 202' and includes mid-beat ECG point calculation via step 502, interpolation between the calculated mid-beat points to reconstruct an estimated baseline via step 504, and removing the estimated baseline from the ECG signal via step 506.

In one embodiment, the QRS complex peak is detected via step 202' on a filtered ECG signal using a narrow bandpass filter to remove low-frequency noises (e.g. baseline wander) and high-frequency noises (e.g. motion artifacts and power-line noise). Once the QRS complex peak detection is complete via step 202', the remaining processing steps 502-506 are done on the original ECG signal detected by the wireless sensor device. The mid-beat ECG point is determined via step 502 as the ECG sample at the time average of two adjacent QRS complex peak times. The mid-beat ECG point typically occurs in the TP-segment of the ECG signal and consists of signal artifacts such as baseline wander. Therefore, by interpolating consecutive mid-beat ECG samples, an estimate of the baseline waveform is obtained via step 504. The estimate of the baseline waveform obtained via step 504 is cancelled by subtraction from the original ECG signal via step 506.

Figure 6:
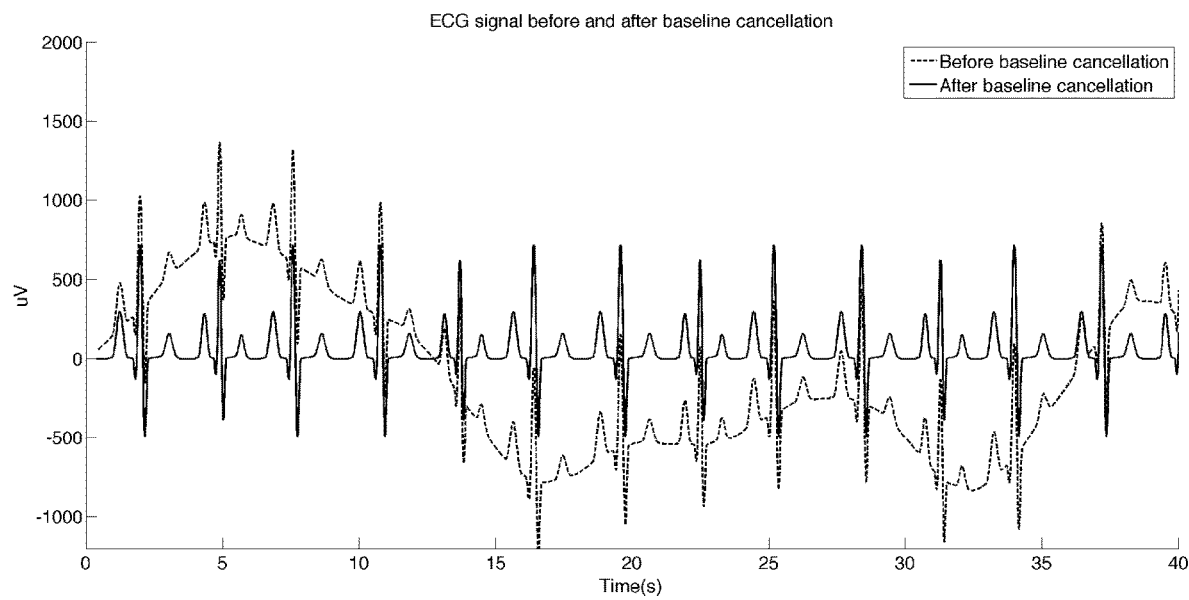
FIG. 6 illustrates a diagram of an ECG signal before and after baseline cancellation in accordance with an embodiment.
Figure 6:
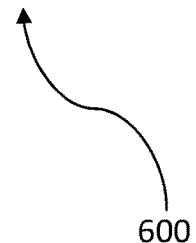

The method 500 takes advantage of the TP-segment of the ECG signal, lying between the end of the T-wave of the previous beat and the start of the P-wave from the current beat, being isoelectric. During this period, heart muscles are at rest and do not generate any electrical signal. Therefore, any EGG reading during the TP segment comes from artifacts other than the ECG signal. FIG. 6 illustrates a diagram 600 of an ECG signal before and after baseline cancellation in accordance with an embodiment. In FIG. 6, the baseline cancellation is achieved using the method 500 that calculates mid-beat ECG values to reconstruct the baseline.

In one embodiment, the resampling via step 206 comprises stretching in time each beat of the ECG signal to create a fixed length for each beat. In one embodiment, the fixed length is a length of LENGTH_REFERENCE_BEAT seconds. The LENGTH_REFERENCE_BEAT is selected to accommodate the lowest heart rate and includes but is not limited to a value of 20 seconds. The resampling via step 206 enables the time aligning of same sections of neighboring beats within the ECG signal including but not limited to P-Wave, T-Wave, and QRS complex sections.

Time-aligned sections of the ECG beats are then denoised by utilizing coherent ensemble denoising via step 212 across aligned beats using appropriate filters designed based on each section's frequency content. This form of ensemble averaging allows a more aggressive noise-reduction in sections of the ECG signal that occupy a lower frequency spectrum/content (e.g. P-Wave, T-Wave, TP segment) without distorting sections with a higher frequency spectrum/content (e.g. QRS complex).

Figure 7:
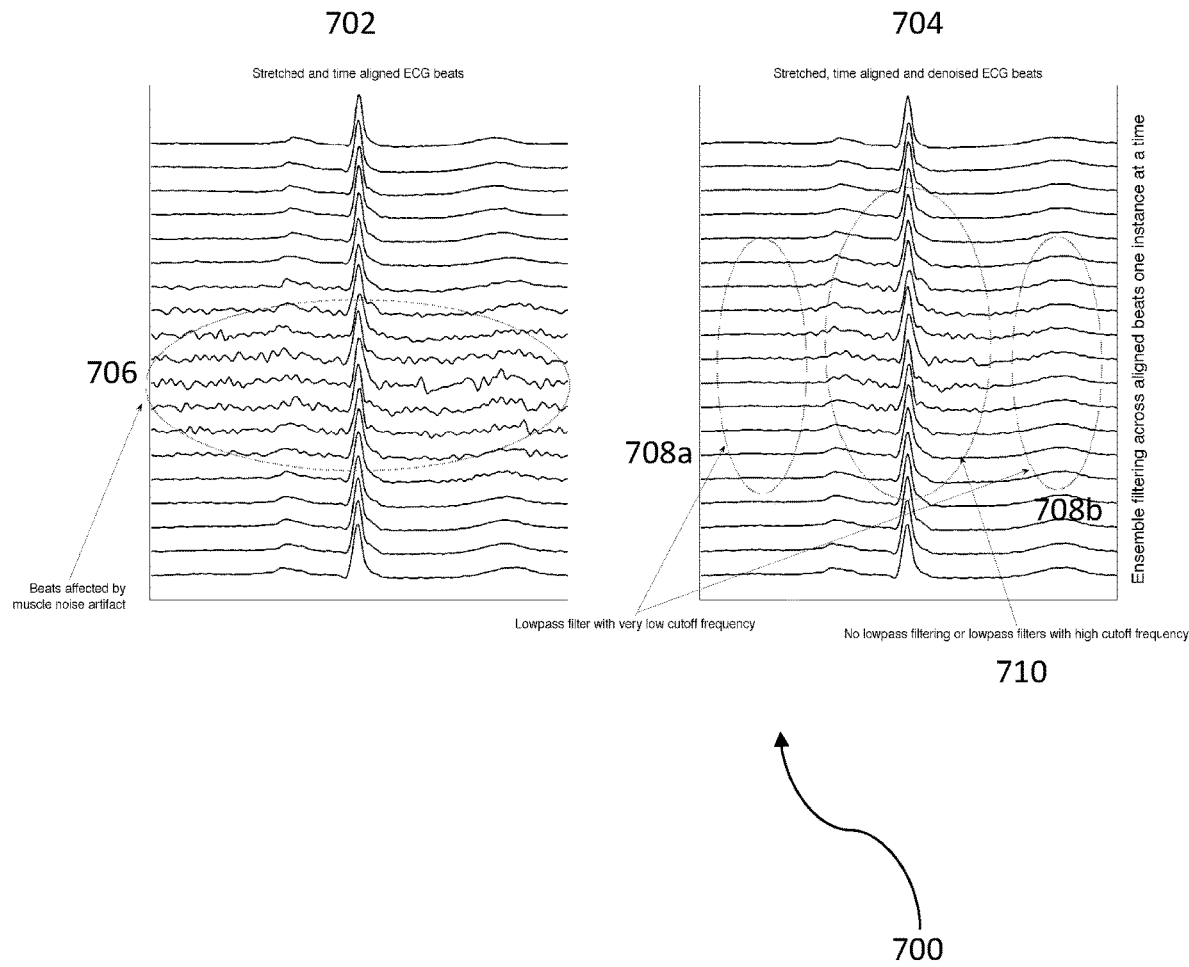
FIG. 7 illustrates a diagram of aligned ECG beats of an ECG signal before and after denoising in accordance with an embodiment.

FIG. 7 illustrates a diagram 700 of aligned ECG beats of an ECG signal before and after denoising in accordance with an embodiment. The diagram 700 includes a first graph 702 depicting stretched and time aligned ECG beats of the ECG signal before denoising and a second graph 704 depicting stretched, time aligned, and denoised ECG beats of the ECG signal with denoising achieved by utilizing ensemble filtering across the aligned beats one instance at a time.

The first graph 702 includes an area 706 where beats of the ECG signal are affected by muscle noise artifact. The second graph 704 includes areas 708a and 708b where a lowpass filter with very low cutoff frequency is utilized to smooth the ECG signal and remove noise and includes an area 710 where no lowpass filtering is utilized or where lowpass filters with high cutoff frequencies are utilized to smooth the ECG signal and remove noise.

Figure 8:
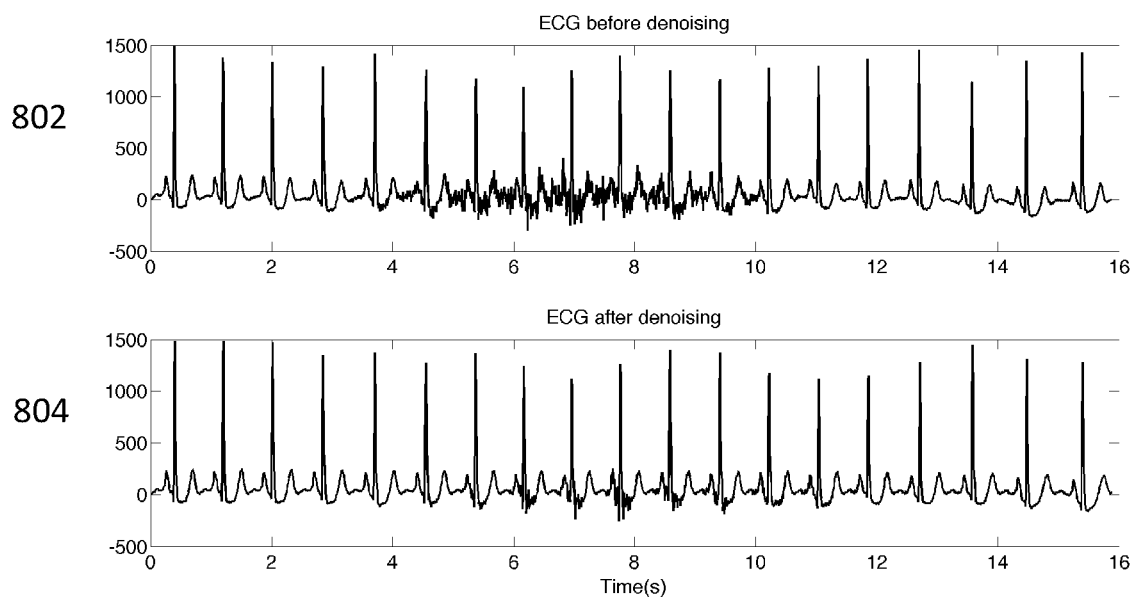
FIG. 8 illustrates a diagram of an ECG signal before and after denoising in accordance with an embodiment.

FIG. 8 illustrates a diagram 800 of an ECG signal before and after denoising in accordance with an embodiment. The diagram 800 includes a first graph 802 depicting an EGG signal before denoising and thus affected by motion artifacts/noise. The diagram 800 includes a second graph 804 depicting the ECG signal after denoising achieved using a method and system in accordance with the present invention. The ECG signal after denoising is smoother and less noisy.

The method 200 for low-distortion denoising relies on a correlation between adjacent heartbeats to reduce noise within the ECG signal detected by the wireless sensor device 100. Therefore, outlier beats of the ECG signal are excluded by the wireless sensor device 100 using a beat selection logic unit that performs beat selection logic for denoising, via step 210, thereby enabling preservation of the abnormal/outlier beats for manual inspection. Examples of outlier beats include but are not limited to atrial premature, premature ventricular contractions (PVCs), and nodal premature beats.

A method and system in accordance with the present invention quantifies the difference between the beats by utilizing time-domain and statistical properties of the beats. Additionally, the method and system in accordance with the present invention identifies whether the difference between the beats is only due to noise, and if so, does not exclude these beats from the denoising process.

In one embodiment, an input to the beat selection logic unit is a user's posture. If the user's posture changes during detection/recording of an ECG signal by a wireless sensor device attached to the user, the position of the user's heart relative to the electrodes of the wireless sensor device may change, thereby changing the ECG features of the ECG signal. Therefore, ECG beats of the ECG signal recorded during two different user postures are not combined together during the low-distortion denoising process carried out by the wireless sensor device. Instead, a beat is used for the low-distortion denoising process and is used for updating a reference beat if the user's posture during the beat is similar to the user's posture during the rest of the beats used by the wireless sensor device to calculate the reference beat. The user's posture is determined using a MEMS device embedded in the wireless sensor device.

In another embodiment, additional inputs to the beat selection logic unit include polarity changes, irregular RR intervals, irregular QRS amplitudes, and statistical changes.

Figure 9:
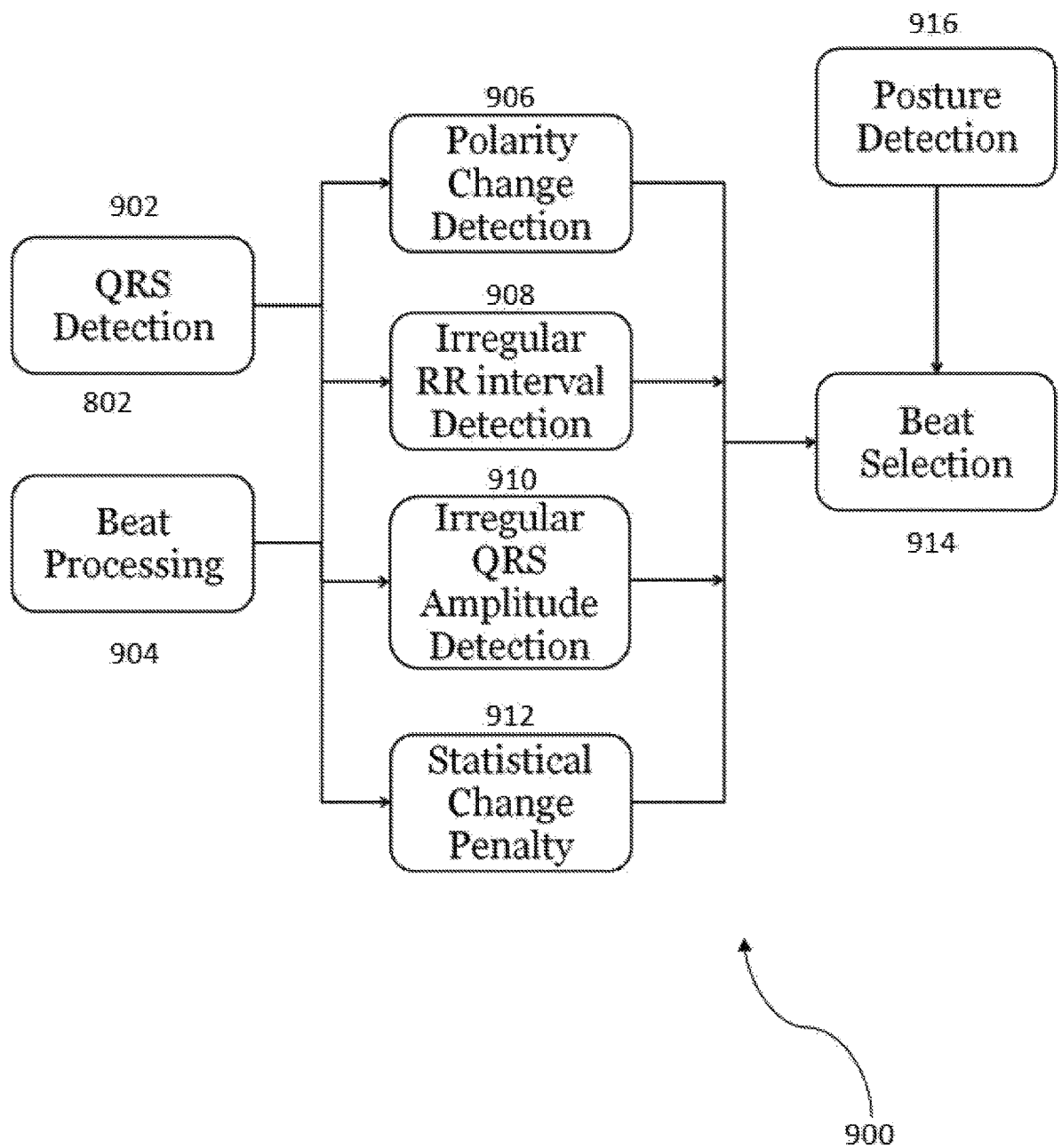
FIG. 9 illustrates a block diagram of beat selection logic for denoising utilized by a wireless sensor device in accordance with an embodiment.

FIG. 9 illustrates a block diagram 900 of beat selection logic for denoising utilized by a wireless sensor device in accordance with an embodiment. The block diagram 900 includes a QRS detection block 902, wherein the wireless sensor device detects an ECG signal of a user of the wireless sensor device and detects QRS complex peaks from the ECG signal, and a beat processing block 904, wherein the wireless sensor device processes beats of the ECG signal for denoising.

The outputs of blocks 902 and 904 both feed into a polarity change detection block 906, an irregular RR interval detection block 908, an irregular QRS amplitude detection block 910, and a statistical change penalty block 912. The outputs of blocks 906-912 feed into a beat selection block 914. Additionally, an output of a posture detection block 916 also feeds into the beat selection block 914.

In the polarity change detection block 906, the wireless sensor device determines whether the polarity of a last N_POLARITY_QRS complex peaks of a detected ECG signal is the same. If yes (the polarity of the last N_POLARITY_QRS complex peaks is the same), the wireless sensor device sets Flag1 to 0. If no (the polarity of the last N_POLARITY_QRS complex peaks is not the same), the wireless sensor device sets Flag1 to 1. In one embodiment, the N_POLARITY value includes but is not limited to 16 beats (heartbeats). The N_POLARITY value is selected to represent a tradeoff between accurately determining the reference beat latency of the ECG denoising process and adapting to large changes in ECG signal morphology.

In the irregular RR interval detection block 908, the wireless sensor device determines whether an RR interval of the detected ECG signal is within P_RR percent of a previous RR interval of the detected ECG signal. If yes (the RR interval is within P_RR percent of the previous RR interval), the wireless sensor device sets Flag2 to 0. If no (the RR interval is not within P_RR percent of the previous RR interval), the wireless sensor device sets Flag2 to 1. In one embodiment, the P_RR percent value includes but is not limited to 25%. A threshold of around 20-25% is frequently used to identify abnormal heartbeats (e.g. arrhythmia processing), In the irregular QRS amplitude detection block 910, the wireless sensor device determines whether a QRS amplitude of the detected ECG signal is within P_QRSA percent of a previous QRS amplitude of the detected ECG signal. If yes (the QRS amplitude is within P_QRSA percent of the previous QRS amplitude), the wireless sensor device sets Flag3 to 0. If no (the QRS amplitude is not within P_QRSA percent of the previous QRS amplitude), the wireless sensor device sets Flag3 to 1. In one embodiment, the P_QRSA value includes but is not limited to 25%. The QRS amplitude threshold is P_QRSA and the value is selected to identify abnormally large or small beats, which may indicate an arrhythmia. Therefore, the P_QRSA threshold is selected as 25% to be similar to the PRR threshold of 25%.

In the posture detection block 916, the wireless sensor device determines whether the user's posture has been the same over a last N_POSTURE beats. If yes (the user's posture is the same over a last N_POSTURE beats), the wireless sensor device sets Flag5 to 0. If no (the user's posture is not the same over the last N_POSTURE beats), the wireless sensor device sets Flag5 to 1. In one embodiment, the N_POSTURE value includes but is not limited to 16 beats (heartbeats). The default N_POSTURE value is selected for reasons similar to the default N_POLARITY value in that the N_POSTURE value is selected to represent a tradeoff between accurately determining the reference beat latency of the ECG denoising process and adapting to large changes in ECG signal morphology.

In one embodiment, the wireless sensor device utilizes the following equations 1-4 for determining the statistical change penalty in the beat selection logic for denoising via block 912:

$$e(n) = r(n) - x(n) \quad (1)$$

$$\frac{\sqrt{\sum_{i=1}^{N} e(n)^2}}{\sqrt{\sum_{i=1}^{N} r(n)^2}} < \text{RMS\_CHANGE\_THRESHOLD} \quad (2)$$

$$e_0 = \frac{1}{N} \sum_{i=1}^{N} e(n) \quad (3)$$

$$\frac{\sum_{i=1}^{N} (e(n) - e_0)^4}{\left(\sum_{i=1}^{N} (e(n) - e_0)^2\right)^2} < \text{KURTOSIS\_THRESHOLD} \quad (4)$$

If equations 2 and 4 are both satisfied, then Flag4 is set to 0. In equation 2, the RMS_CHANGE_THRESHOLD value includes but is not limited to 0.2. In equation 4, the KURTOSIS_THRESHOLD value includes but is not limited to 6. In one embodiment, the default values for the RMS_CHANGE_THRESHOLD and the KURTOSIS_THRESHOLD are determined by analyzing several ECG signals with and without artifacts. In equations 1-4, N is the number of ECG samples in one ECG reference beat; r(n) is a reference beat consisting of N samples or LENGTH_REFERENCE_BEAT seconds; x(n) is the latest beat after removing baseline and stretching to LENGTH_REFERENCE_BEAT samples.

In one embodiment, the wireless sensor device calculates a root mean square difference of the latest beat versus the reference beat using equation 2 to determine whether the root mean square difference is smaller than a first threshold (e.g. the RMS_CHANGE_THRESHOLD). If the inequality in equation 2 is satisfied (the root mean square difference is smaller than the RMS_CHANGE_THRESHOLD), the current beat is not significantly different from the reference beat in the root-mean-square sense. The wireless sensor device calculates the Kurtosis of the difference between the latest beat and the reference beat using equation 4 to determine that the difference between the latest beat and the reference beat is due to noise and not a change in features of the beat.

The wireless sensor device compares the calculated Kurtosis to a second threshold (e.g. KURTOSIS_THRESHOLD). If the calculated Kurtosis is lower than the KURTOSIS_THRESHOLD, then the difference between the latest beat and the reference beat is determined by the wireless sensor device to be due to noise because Gaussian or uniformly distributed noise have a small Kurtosis. However, if the calculated Kurtosis is larger than the KURTOSIS_THRESHOLD, then the difference between the latest beat and the reference beat is determined to be due to a structural change in the ECG signal.

In one embodiment, if the wireless sensor device sets Flag1, Flag2, Flag3, Flag4, and Flag5 all to 0 after utilizing the beat selection logic for denoising of FIG. 9, the latest beat is denoised by the wireless sensor device and then the wireless sensor device updates the reference beat using the latest beat. The latest beat is denoised to reduce the noise using appropriate parameters for each section of the beat. The wireless sensor device utilizes the latest beat to update the reference beat by providing samples of the latest beat to a corresponding ensemble averaging filter using the coherent ensemble denoising via step 212. Outputs of an N number of ensemble averaging filters are cascaded in order to create the reference beat.

In one embodiment, each section of the beat is denoised by applying an ensemble filter that processes the current section as well as the corresponding sections of the previously stored beats. The ensemble filter parameters vary depending on the location of the section of the beat under consideration. For example, sections near the QRS complex do not undergo significant filtering, whereas sections near the mid-beat region undergo significant lowpass filtering. The filter parameters are varied so that the ECG signal is denoised while preserving most of the morphological features near the QRS complex.

Figure 10:
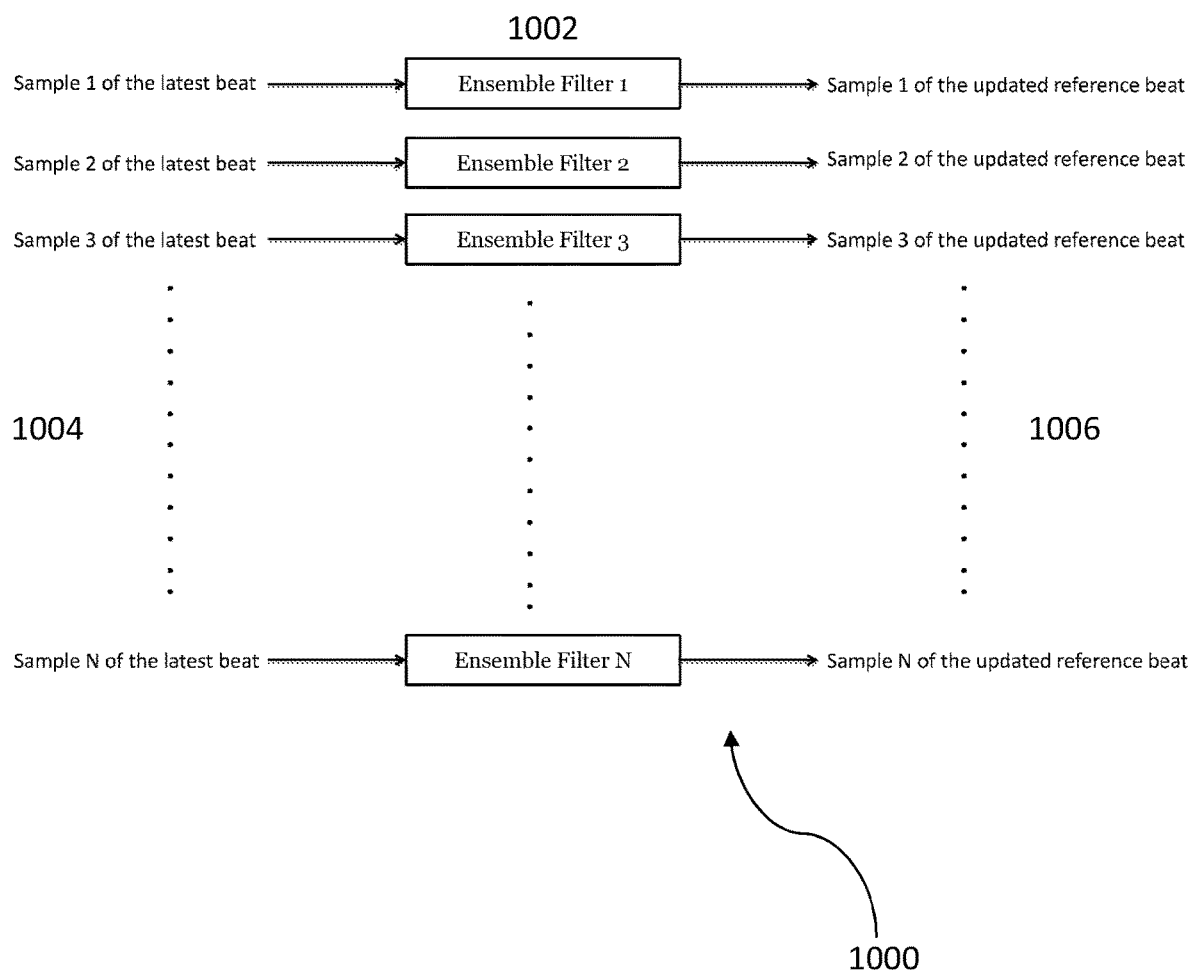
FIG. 10 illustrates a diagram for updating a reference beat using ensemble averaging filters in accordance with an embodiment.

FIG. 10 illustrates a diagram 1000 for updating a reference beat using ensemble averaging filters in accordance with an embodiment. The diagram 1000 includes a plurality of ensemble averaging filters 1002 that receive a plurality of samples of a latest beat 1004 as inputs. The plurality of ensemble averaging filters 1002 output a plurality of samples of an updated reference beat 1006. For example, sample k of the reference beat is essentially a lowpass filtered version of sample k from the beats that pass the beat selection criteria (e.g. all of Flag1, Flag2, Flag3, Flag4 and Flag5 are set to 0).

In this embodiment, if any of Flag1, Flag2, Flag3, Flag4, or Flag5 are set to 1 (or not set to 0) after utilizing the beat selection logic for denoising of FIG. 9, the wireless sensor device resets the reference beat and does not perform denoising on the latest beat. The wireless sensor device resets the reference beat by overriding values of the reference beat with values of the latest beat.

In one embodiment, the resampling to the original RR interval via step 214 comprises time-scaling the denoised beat back to its original length. The resampling accomplished via step 214 is the inverse of the resampling accomplished via step 206. For example, if step 206 stretched the current beat to a large duration, step 214 will shrink the current beat back to the original duration. Note that the denoised beat is time-scaled back to the length of the original beat by the wireless sensor device if the denoising process is performed on the beat. If the beat is not denoised because the beat selection criteria is not satisfied, the non-denoised beat is time-scaled back to the length of the original beat. If the wireless sensor device determines that the reference beat should be reset, the reference beat is overwritten by the latest beat.

A method and system in accordance with the present invention provide for lo distortion denoising of an ECG signal. In one embodiment, the method comprises determining at least one beat of the ECG signal for denoising using a beat selection logic and denoising the at least one beat using at least one ensemble averaging filter. In this embodiment, the method includes detecting at least one QRS peak of the ECG signal using a narrow bandwidth filter and cancelling baseline wander of the ECG signal using interpolation between values of TP segments of consecutive beats of the ECG signal.

In this embodiment, the cancelling further comprises calculating a plurality of mid-beats of the ECG signal, interpolating between the plurality of mid-beats to reconstruct a baseline, and removing the baseline from the ECG signal. The method includes resampling a plurality of beats of the ECG signal to create a predetermined length for each beat of the plurality of beats, wherein the resampling time aligns same sections of neighboring beats of the plurality of beats.

In this embodiment, the beat selection logic is used to exclude outlier beats of the ECG signal from the denoising and the beat selection logic includes any of polarity change detection, irregular RR interval detection, irregular ORS amplitude detection, statistical change penalties, and posture detection. The method includes determining whether a difference between at least two beats of the ECG signal is due only to noise, wherein the at least two beats are not excluded from the denoising if the difference between the at least two beats is due only to noise.

In this embodiment, the determining further comprises calculating a Kurtosis of a difference between a latest beat and a reference beat and comparing the calculated Kurtosis to a Kurtosis threshold. The at least one ensemble averaging filter is used to calculate the reference beat. The method includes time-scaling the at least one denoised beat back to an original length.

As above described, a method and system in accordance with the present invention provides low-distortion denoising that reduces baseline wander, motion artifacts, and muscle noise in an ECG signal of a user of a wireless sensor device without distorting or altering the basic features of the ECG signal that are valuable. The wireless sensor device detects an ECG signal of the user and performs low-distortion denoising by detecting QRS complex peaks, baseline cancellation, resampling via stretching beats, ECG buffering by aligning stretched beats in time, using beat selection logic to determine which beats are eligible for denoising, using coherent ensemble averaging for the denoising, and then resampling back to original lengths.

A method and system for low-distortion denoising of an ECG signal by a wireless sensor device have been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or calculator-readable medium. The software application provides instructions that enable the processor to perform the functions described herein.

Furthermore, embodiments may take the form of a calculator program product accessible from a calculator-usable or calculator-readable medium providing program code for use by or in connection with a calculator or any instruction execution system. For the purposes of this description, a calculator-usable or calculator-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a calculator-readable medium include a semiconductor or solid state memory, magnetic tape, a removable calculator diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method of beat selection logic for denoising of an ECG signal by a wireless sensor device including a memory and a processor, the memory storing executable instructions that, in response to execution by the processor, causes the wireless sensor device to perform operations comprising:
   detecting an ECG signal of a user of the wireless sensor device;
   determining a selection of beats for denoising based on a collective of output flags from at least one of:
      a first output flag corresponding to a polarity change detection,
      a second output flag corresponding to an irregular RR interval detection,
      a third output flag corresponding to an irregular QRS amplitude detection,
      a fourth output flag corresponding to a statistical change penalty detection, and
      a fifth output flag corresponding to a posture change detection applied to the ECG signal detected by the wireless sensor device;
   in response to all five output flags being set, selecting a latest beat for denoising; and
   in response to any of the five output flags not being set, not performing denoising on the latest beat.

2. The method of claim 1, further comprising:
   determining the polarity change detection by whether a polarity of a last N_POLARITY QRS complex peaks of the detected ECG signal is the same; and
   in response to the polarity of the last N_POLARITY QRS complex peaks is the same, setting the first output flag.

3. The method of claim 1, further comprising:
   determining the irregular RR interval detection by whether an RR interval of the detected ECG signal is within a P_RR percent of a previous RR interval of the detected ECG signal; and
   in response to the RR interval is within P_RR percent of the previous RR interval, setting the second output flag.

4. The method of claim 1, further comprising:
   determining the irregular QRS amplitude detection by whether a QRS amplitude of the detected ECG signal is within a P_QRSA percent of a previous QRS amplitude of the detected ECG signal; and
   in response to the QRS amplitude is within P_QRSA percent of the previous QRS amplitude, setting the third output flag.

5. The method of claim 1, further comprising:
   determining the statistical change penalty detection by satisfying two conditions:
      a first condition is satisfied if a root mean square difference of a latest beat versus a reference beat is smaller than a first threshold, and
      a second condition is satisfied if a calculated Kurtosis is lower than a second threshold; and
   in response to satisfying the first condition and the second condition, setting the fourth output flag.

6. The method of claim 1, further comprising:
   determining the posture change detection by whether the user's posture has been the same over a last N_POSTURE beats; and
   in response to the user's posture is the same over a last N_POSTURE beats, setting the fifth output flag.

7. The method of claim 2, further comprising: in response to the polarity of the last N_POLARITY QRS complex peaks is not the same, not setting the first output flag.

8. The method of claim 3, further comprising: in response to the RR interval is not within P_RR percent of the previous RR interval, not setting the second output flag.

9. The method of claim 4, further comprising: in response to the QRS amplitude is not within P_QRSA percent of the previous QRS amplitude, not setting the third output flag.

10. The method of claim 9, wherein the QRS amplitude threshold is P_QRSA and the value is selected to identify abnormally large or small beats to indicate an arrhythmia.

11. The method of claim 5, further comprising: in response to at least one of the two conditions not being satisfied, not setting the fourth output flag.

12. The method of claim 6, further comprising: in response to the user's posture is not the same over the last N_POSTURE beats, not setting the fifth output flag.

13. The method of claim 1, wherein the N_POSTURE value includes 16 beats.

14. The method of claim 13, wherein a default N_POSTURE value is selected to represent a tradeoff between accurately determining the reference beat latency of the ECG denoising process and adapting to large changes in ECG signal morphology.

15. The method of claim 1, wherein the latest beat is denoised to reduce the noise using appropriate parameters for each section of the beat.

16. The method of claim 1, wherein the latest beat is utilized to update the reference beat by providing samples of the latest beat to a corresponding ensemble averaging filter using the coherent ensemble denoising.

17. The method of claim 6,
   wherein outputs of an N number of ensemble averaging filters are cascaded in order to create the reference beat, and
   wherein each section of the beat is denoised by applying an ensemble filter that processes the current section as well as the corresponding sections of the previously stored beats.

18. The method of claim 17, wherein the ensemble filter parameters vary depending on the location of the section of the beat under consideration.

19. The method of claim 18, wherein the varying includes sections near the QRS complex do not undergo significant filtering, and sections near the mid-beat region undergo significant lowpass filtering.

20. A non-transitory computer-readable medium storing executable instructions that, in response to execution, cause a computer to perform a beat selection logic for denoising of an ECG signal operations comprising:
   detecting an ECG signal of a user of the wireless sensor device;
   determining a selection of beats for denoising based on a collective of output flags from at least one of:
      a first output flag corresponding to a polarity change detection,
      a second output flag corresponding to an irregular RR interval detection,
      a third output flag corresponding to an irregular QRS amplitude detection,
      a fourth output flag corresponding to a statistical change penalty detection, and
      a fifth output flag corresponding to a posture change detection applied to the ECG signal detected by the wireless sensor device;
   in response to all five output flags being set, selecting a latest beat for denoising; and
   in response to any of the five output flags not being set, not performing denoising on the latest beat.

* * * * *